US00PP26595P2

(12) United States Plant Patent
Hansen

(10) Patent No.: US PP26,595 P2
(45) Date of Patent: Apr. 5, 2016

(54) ***SEDUM* PLANT NAMED 'FIRECRACKER'**

(50) Latin Name: *Sedum hybrida*
Varietal Denomination: Firecracker

(71) Applicant: Christopher M. Hansen, Holland, MI (US)

(72) Inventor: Christopher M. Hansen, Holland, MI (US)

( * ) Notice: Subject to any disclaimer, the term of this patent is extended or adjusted under 35 U.S.C. 154(b) by 146 days.

(21) Appl. No.: 13/998,807

(22) Filed: Dec. 10, 2013

(51) Int. Cl.
*A01H 5/02* (2006.01)

(52) U.S. Cl.
USPC ..... Plt./479

(58) Field of Classification Search
USPC ..... Plt./479
See application file for complete search history.

*Primary Examiner* — Keith Robinson
(74) *Attorney, Agent, or Firm* — Penny J. Aguirre

(57) ABSTRACT

A new cultivar of *Sedum* plant named 'Firecracker' that is characterized by its very shiny foliage that is deep cherry-red in color with the color retained in spring, summer and fall, its very heavy branching with the stems forming a mounded plant habit with no opening in the center or flopping of stems, its large pink flower heads, its very heavy vegetative bud production during winter dormancy, and its high resistance to *Sedum* foliage blight.

2 Drawing Sheets

Botanical classification: *Sedum hybrida.*
Variety denomination: 'Firecracker'.

BACKGROUND OF THE INVENTION

The present invention relates to a new and distinct cultivar of *Sedum* plant of hybrid origin known as *Sedum* 'Firecracker' and will be referred to hereinafter by its cultivar name, 'Firecracker'. The new cultivar of *Sedum* is a hardy herbaceous perennial grown for use as a landscape and container plant with particular use as a groundcover.

'Firecracker' arose from an ongoing breeding program conducted by the Inventor in Hudsonville, Mich., USA. The goal of this particular breeding program was to develop a new groundcover type cultivar of *Sedum* with dark cherry red foliage that is retained throughout the growing season combined with a compact, mounded plant habit without the tendency to flop.

The Inventor made a cross in July 2009 between two unnamed plants from the Inventor's breeding program as both the female (a low growing hybrid) and male parent (a tall growing hybrid). 'Firecracker' was selected as a single unique plant in September 2010 amongst the seedlings that resulted from the above cross.

Asexual propagation of the new cultivar was first accomplished by tip stem cuttings in July of 2010 in Hudsonville, Mich. Asexual propagation by tip stem cuttings has determined the characteristics of the new cultivar are stable and reproduced true to type in successive generations.

SUMMARY OF THE INVENTION

The following traits have been repeatedly observed and are determined to be the characteristics of the new cultivar. These attributes in combination distinguish 'Firecracker' as a unique cultivar of *Sedum.*

1. 'Firecracker' exhibits very shiny foliage that is deep cherry-red in color with the color retained in spring, summer and fall.

2. 'Firecracker' exhibits very heavy branching with the stems forming a mounded plant habit with no opening in the center or flopping of stems.
3. 'Firecracker' exhibits pink flower heads that are large for a groundcover type *Sedum*; an average of 10 cm in diameter.
4. 'Firecracker' exhibits very heavy vegetative bud production with over 50 buds in a 30-cell plug when entering winter dormancy; unusual for a young small plant of this type of *Sedum.*
5. 'Firecracker' has been observed to be highly resistant to *Sedum* foliage blight.

The female parent of 'Firecracker' differs from 'Firecracker' in having an overall plant size that is 70 percent smaller, in having smaller leaves, in having foliage that is blue-gray in color, and in having smaller flowers (4 cm in diameter). The male parent differs from 'Firecracker' in having an overall plant size that is 70 percent larger, in having an upright plant habit, in having foliage that is blue-gray in color, and in having larger leaves. 'Firecracker' can also be most closely compared to the cultivars 'Cherry Tart' (U.S. Plant Pat. No. 24,603) and 'Voodoo' (not patented). Both cultivars are similar to 'Firecracker' in being groundcover-type *Sedums* and in having foliage that is red in color. 'Cherry Tart' differs from 'Firecracker' in having larger leaves, in having less dense branching, in forming half as many dormant eyes during the winter, and in having 50 percent more flower stems and blooms. 'Voodoo' differs from 'Firecracker' in having smaller leaves with more heavily serrate margins, in having a blooming period that begins two months earlier, in having smaller flowers, in having thinner foliage that has less substance, and in being a seed strain with great variability.

BRIEF DESCRIPTION OF THE DRAWINGS

The accompanying colored photographs illustrate the overall appearance and distinct characteristics of the new *Sedum.*

The photograph in FIG. 1 was taken of a 3 month-old plant of 'Firecracker' as grown outdoors in a five-inch container in Hudsonville, Mich. and provides a view of the young foliage and heavy branching of an un-pinched plant of 'Firecracker'.

Figure 1:
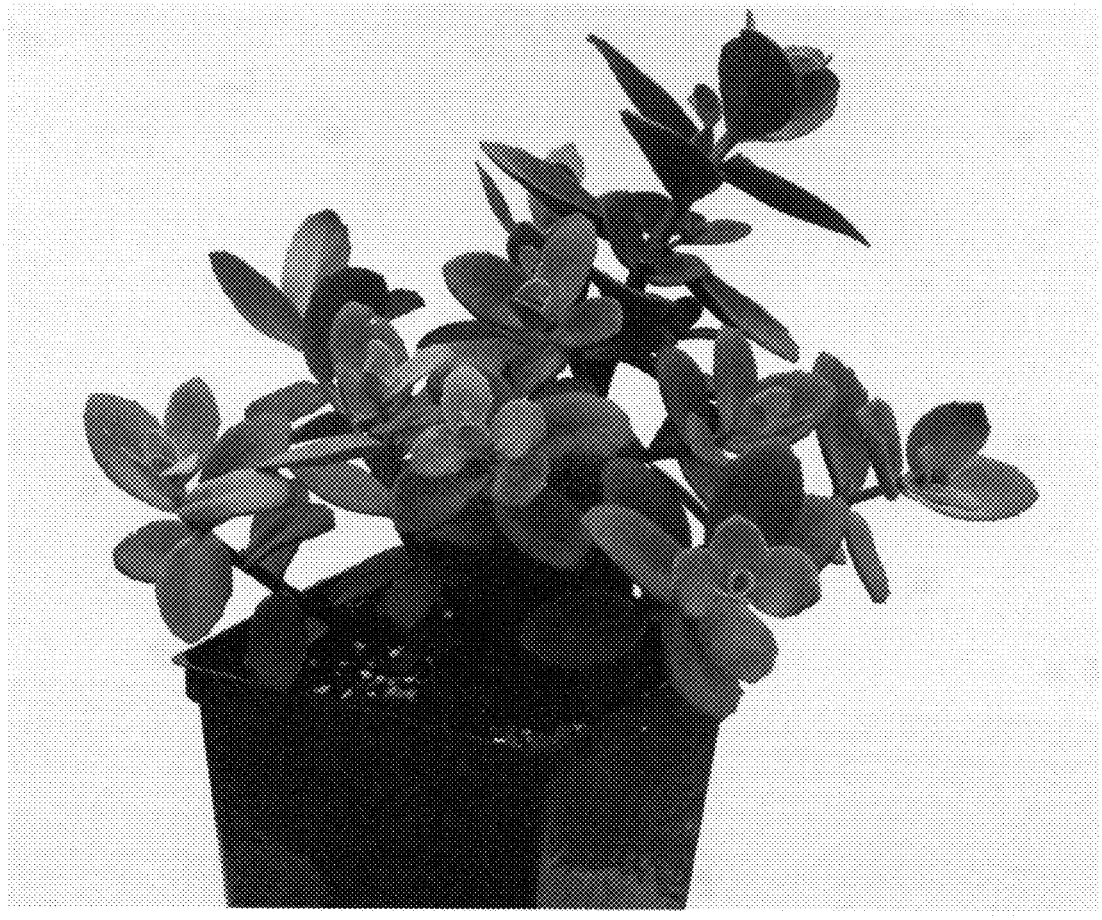
Figure 2:
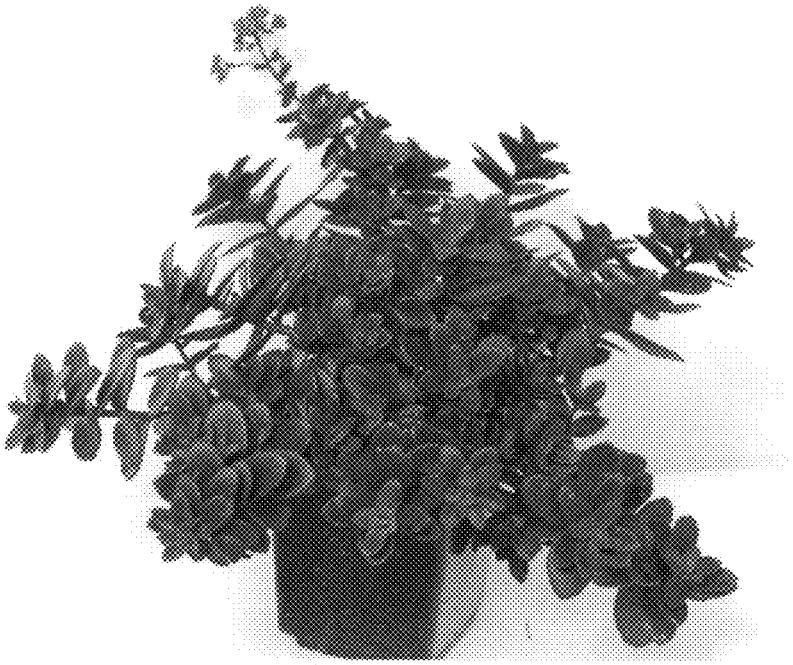
Figure 3:
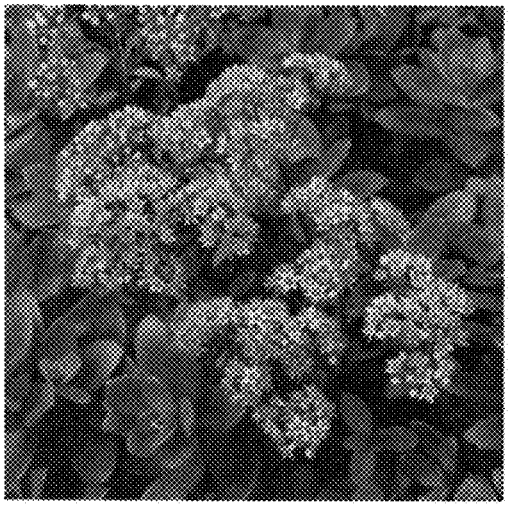
Figure 4:
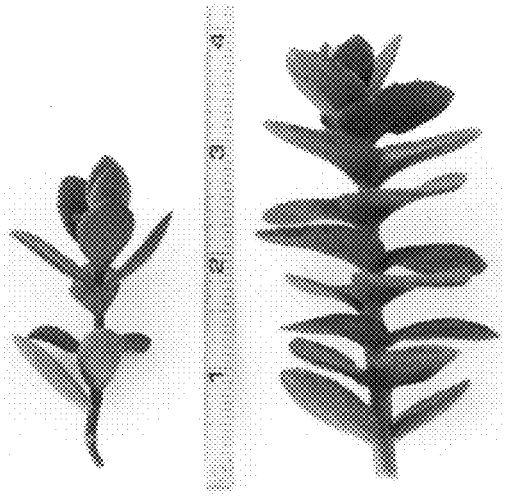

The photographs in FIG. 2, FIG. 3, and FIG. 4 were taken of one year-old plants of 'Firecracker'.

The photograph in FIG. 2 provides a side view of the mature foliage color of 'Firecracker'.

The photograph in FIG. 3 provides a view of the flower heads of 'Firecracker'.

The photograph in FIG. 4 provides a view of the dormant buds of 'Firecracker'.

The colors in the photographs may differ slightly from the color values cited in the detailed botanical description, which accurately describe the colors of the new *Sedum*.

DETAILED BOTANICAL DESCRIPTION

The following is a detailed description of the new cultivar as observed on one year-old plants of 'Firecracker' as observed throughout the growing season in a garden in full sun in New Hope, Minn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—An average of 5 weeks in mid to late summer in Michigan.

*Plant type*.—Herbaceous perennial.

*Plant habit*.—Compact, tightly mounded without the centers opening, flower stems that are held upright and do not flop.

*Height and spread*.—Reaches an average of 15 cm in height and about 46 cm in spread.

*Hardiness*.—At least in U.S.D.A. Zones 4 to 9.

*Diseases*.—Observed to be highly resistant to *Sedum* foliage blight (*Colletotrichum* spp.).

*Root description*.—Fibrous and 174D in color.

*Propagation*.—Tip stem cuttings.

*Root development*.—An average of ten days for root initiation and about three weeks to produce a young rooted plant.

*Growth rate*.—Vigorous; very heavy vegetative bud production with over 50 buds in a 30-cell plug when entering winter dormancy.

*Drought tolerance*.—Moderate.

Stem description:

*Stem shape*.—Round.

*Stem size*.—Up to 10 cm in length and an average of 1 cm in width.

*Internode length*.—Average of 1 cm.

*Stem color*.—Young; 187A, mature; 200A with very fine striations of 164A.

*Stem surface*.—Glabrous and shiny.

*Branching habit*.—Basal and laterals from each node on stem.

Foliage description:

*Leaf shape*.—Elliptic to ovate.

*Leaf division*.—Simple.

*Leaf arrangement*.—Whorled (sometime opposite).

*Leaf base*.—Slightly cordate.

*Leaf apex*.—Broadly acute.

*Leaf venation*.—Not conspicuous, color matched leaf color.

*Leaf margins*.—Crenate to slightly serrated on upper half of lower stems leaves, mostly entire near apex and on peduncles.

*Leaf attachment*.—Sessile.

*Leaf presence and orientation*.—Held at an average angle between 45° and 50° to stem.

*Leaf substance*.—Thick, succulent.

*Leaf surface texture* (*upper and lower surface*).—Glandular and slightly glaucous when young and becoming shiny when mature.

*Leaf color*.—Spring; young upper and lower surface, blend of 137A and 144A, tip becoming 187C, mature upper and lower surface a blend of 187A and 187C, summer; young upper surface 187A, base 143A, young lower surface 187B suffused with N137A, margin towards the base 144B, mature upper surface; 187A, with a slight sheen overlay of 189B, mature lower surface 187C, with a sheen overlay of 189B.

*Leaf size*.—An average of 1.8 cm in length and 1.3 cm cm in width.

Flower description:

*Inflorescence type*.—Dense, slightly rounded cymes with an average of 8 terminal forked branches at terminus and upper lateral nodes.

*Inflorescence size*.—An average of 10 cm in depth and width.

*Lastingness of inflorescence*.—At least one month.

*Flower type*.—Perfect, spreading, 5-starred.

*Flower number*.—An average of 80 flowers per branched cyme, about 800 flowers per stem.

*Flower fragrance*.—None.

*Flower buds*.—Conical in shape, about 4 mm length and 3 mm in diameter, ribbed surface, color; base is 158D, mid-section is N78C, tip is N78A.

*Flower size*.—About 5 mm in depth and 4 mm in diameter.

*Peduncles*.—Round in shape, up to 2 cm in length, an average of 2 mm in width, 185A in color, glabrous and shiny surface, secondary peduncle; 2 cm in length and 1 mm in width, 184B in color, both strong in strength, peduncle leaves; an average of 2 per individual cyme, elliptic in shape, an average of 1.5 cm in length and 1 cm in width, 187A in color, glaucous surface.

*Pedicels*.—Round in shape, up to 5 mm in length, an average of 1 mm in width, a blend of 184C, N186C and N170C, strong in strength, glabrous surface, pedicel leaves; 3 mm in length and 2 mm in width, N186C in color.

*Sepals*.—5, 2 mm in length and 1 mm in width, lanceolate in shape, 183A in color, entire margin, narrowly acute apex, fused base, glaucous on both surfaces.

*Petals*.—5, spreading, about 3 mm in length and 2 mm in width, lanceolate in shape, truncate base, acute apex, entire margin, color of inner and outer surfaces when opening and mature; translucent, a blend of N74C and N74A, glabrous surfaces on both surfaces.

Reproductive organs:

*Pistils*.—5, showy, held erect, about 3 mm in length, stigma; 0.5 mm in length and 83A in color, style; 2 mm in length, 1 mm in width, lanceolate in shape and color N74, ovary; small, single celled and translucent in color.

*Stamens*.—10, about 2 mm in length, filament; very fine and a blend of N74C and N74A in color, anther;

heart-shaped, about 0.5 mm in length and width and 203A in color, pollen is low in quantity and to minimal for color determination.

*Fruit and seed*.—Seed production was not observed.

It is claimed:

1. A new and distinct variety of *Sedum* plant named 'Firecracker' as described and illustrated herein.

* * * * *